United States Patent
Cohen et al.

(10) Patent No.: US 7,879,114 B2
(45) Date of Patent: Feb. 1, 2011

(54) METHOD AND KIT FOR MODIFYING THE COLORATION OF KERATINOUS FIBRES

(75) Inventors: Moty Cohen, Laval (CA); Dulce Cristina Almeida Da Silva, Pierrefonds (CA)

(73) Assignee: 6569048 Canada Inc., Laval, Quebec (CA)

( * ) Notice: Subject to any disclaimer, the term of this patent is extended or adjusted under 35 U.S.C. 154(b) by 0 days.

(21) Appl. No.: 12/856,153

(22) Filed: Aug. 13, 2010

(65) Prior Publication Data

US 2010/0299847 A1    Dec. 2, 2010

Related U.S. Application Data

(63) Continuation of application No. 11/661,593, filed on Sep. 25, 2007, which is a continuation of application No. PCT/CA2005/001339, filed on Sep. 1, 2005.

(30) Foreign Application Priority Data

Sep. 9, 2004    (CA) .................................. 2481140

(51) Int. Cl.
*A61Q 5/10* (2006.01)
(52) U.S. Cl. ..................... 8/405; 8/406; 8/431; 8/432; 8/552; 132/202; 132/208
(58) Field of Classification Search ............... 8/405, 8/406, 431, 432, 552; 132/202, 208
See application file for complete search history.

(56) References Cited

U.S. PATENT DOCUMENTS

| | | | |
|---|---|---|---|
| 3,986,825 A | 10/1976 | Sokol | |
| 4,010,872 A | 3/1977 | Lozano et al. | |
| 4,511,360 A | 4/1985 | Monnais et al. | |
| 6,706,077 B2 | 3/2004 | Bhagyalakshmi et al. | |
| 2002/0179109 A1 | 12/2002 | Lenzi-Brangi et al. | |
| 2003/0154562 A1 | 8/2003 | Sarojini et al. | |
| 2004/0237218 A1* | 12/2004 | Marsh et al. ................... | 8/405 |

FOREIGN PATENT DOCUMENTS

| | | |
|---|---|---|
| EP | 0443 740 A2 | 8/1991 |
| EP | 1 153 598 | 1/2006 |
| JP | 2005-041820 | 2/2005 |
| WO | WO 2005/002533 | 1/2005 |
| WO | WO 2005/002534 | 1/2005 |
| WO | WO 2006/026851 A1 | 3/2006 |

OTHER PUBLICATIONS

English language translation of Sep. 14, 2009 Office Action in Israeli counterpart application.
International Search Report in related patent application No. PCT/CA2010/000795 mailed Jul. 27, 2010.

* cited by examiner

*Primary Examiner*—Eisa B Elhilo
(74) *Attorney, Agent, or Firm*—Arent Fox LLP

(57) ABSTRACT

A method for permanently modifying a color of keratinous fibres which comprises the steps of:
  first providing a mixture of three compositions A, B and C, wherein said composition A comprises at least a reducing agent and optionally a coloring compound, said composition B comprises at least an alkalizing compound and said composition C comprises at least an oxidizing compound;
  applying said mixture to keratinous fibres for a suitable period of time for modifying the color of said keratinous fibres; and
  removing said mixture from said keratinous fibres.

22 Claims, No Drawings

METHOD AND KIT FOR MODIFYING THE COLORATION OF KERATINOUS FIBRES

CROSS-REFERENCE TO RELATED APPLICATION

This application is a Continuation of U.S. patent application Ser. No. 11/661,593, filed Sep. 25, 2007, which is a 371 National Phase of PCT/CA2005/001339, filed Sep. 1, 2005, which claims priority to Canadian Patent Application No. 2,481,140, filed Sep. 9, 2004. The entire contents of each of the above-identified applications are hereby incorporated by reference in their entirety.

FIELD OF THE INVENTION

The present invention relates to the field of coloring/decoloring keratinous fibres and more specifically to a method for permanently modifying the color of keratinous fibres. The method of the invention comprises a plurality of compositions, which are combined together and applied onto keratinous fibres so as to color and/or decolor it. The present invention also relates to a kit comprising such compositions for modifying the color of keratinous fibres.

BACKGROUND OF THE INVENTION

A large majority of persons, both women and more recently men, color their hair so as to either cover grey or permanently modify their natural hair color.

A variety of chemical preparations are available and commonly used to change the natural characteristics of hair. Color and style are typically changed using dyes, bleaches and permanent-waving preparations. For example, hair color may be non-permanently (i.e. temporarily), semi-permanently (i.e. lasting several days only) or permanently (i.e. lasting until hair re-grows but fading occurs after four to six weeks) changed depending on the particular coloring compositions employed. These chemical preparations can damage hair.

Permanent color requires harsher conditions to efficiently lighten natural pigment and swell the hair, causing cuticles to open. It may be achieved by making use of oxidative dyes, bleaching techniques or using a combination of the both simultaneously. Indeed, oxidative hair dyes are widely used in the hair industry since they provide permanent color to the hair, generally. Upon these harsh conditions, certain physical properties of the hair are altered resulting in dry hair.

Permanent hair dye products usually comprise two components, namely a formulation containing an alkaline agent and dye intermediates and another containing an oxidant such as hydrogen peroxide and other chemical agents. When these types of products are to be used, the two components are mixed together and the so obtained mixture is immediately applied onto any type of hair, and such is done without taking into consideration whether or not the person's hair is damaged, resistant and/or previously chemically treated.

In this connection, known to the Applicant is a plurality of applications and/or patents relating to the field of semi- or permanent hair colorations.

Briefly, European patent application EP-A-1 153 598 discloses a two- and three-part hair dye. In the two-part hair dye, the first part contains an alkali agent and a direct dye; and the second part contains hydrogen peroxide. In the three-part hair dye, the first part contains an alkali agent, the second part contains hydrogen peroxide and the third part contains a direct dye. In either of these dyes, the first part contains a first direct dye (A) selected from a series of very precise chemical formulae; and a second direct dye (B) selected from Basic Blue 99, Basic Blue 47, Disperse Blue 1, Disperse Blue 3, Disperse Blue 7, Disperse Blue 72, Disperse Violet 1, Disperse Violet 4, Disperse Violet 15 and Disperse Violet 27. These hair dyes are capable of dyeing the hair in a natural, deep, brown to black color tone while bleaching the hair.

United States publication no. US 2002/0179109 A1 discloses a substantially ammonia free hair bleach product. More specifically, the hair bleach product contains a hydrogen peroxide developer; a powder activator containing a mixed persulfate oxidizing system, and a monoethanolamine alkalizing agent. It is worth mentioning that this hair bleach product only operates in conditions wherein the pH is about 10 to 12.

United States publication no. US 2003/0154562 A1 discloses a method for treating hair. More precisely, the method consists of three steps, wherein the first step requires contacting a person's hair with a substantially inactive mixture of oxidative hair dye precursors; allowing the mixture to remain in the hair for a period of about 30 seconds to about 60 minutes; and then applying a developer to the hair in order to achieve long lasting hair color change. Contrarily to the invention described later on in the present application, the aforementioned US publication requires that the coloring components be independently applied onto hair so that the precursors have sufficient time to diffuse the colorants onto the hair.

U.S. Pat. No. 6,706,077 discloses a coloring system for hair and/or skin comprises at least three separately packaged components:
  a) a thio compound capable of breaking the S—S bond between cysteine residues, and an alkaline reagent;
  b) a material and/or extract obtainable from the Mucuna plant; and
  c) an oxidizing agent.

U.S. Pat. No. 6,440,177 B1 discloses a single-step process and composition of hair bleach, which can lighten hair up to seven levels. This outcome is achieved by adding to the bleach mixture, a solution containing basic dye molecules, which is stable in the bleach. These dyes fall into the class of water-soluble basic azo compounds.

PCT patent applications WO 2005/002533 A1 and WO 2005/002534 A1 disclose a method for coloring hair to provide more vibrant, natural and long-lasting color. This outcome is achieved by carrying out the following sequential steps:
  Contacting the hair with a dye precursor mixture which comprises a primary intermediate having a pKa in the range from about 3 to about 10 and optionally a coupler having a pKa in the range from about 3 to about 10. It is specified that the pH of the precursor mixture is selected such that less than 50% of the molecules comprising the primary intermediate and the coupler are in their anionic form when they first contact the hair.
  Applying a means for aligning the hair and distributing the dye precursor mixture over the hair (in WO 2005/002533 A1 only).
  Contacting the hair with a developer mixture capable of inducing oxidation of primary intermediate and coupler in the precursor mixture that is in contact with the hair to form colored species.

Generally speaking, a drawback of using these types of hair coloring systems mentioned hereinabove is that they contain a high concentration of dye intermediates combined with strong alkaline agents and such in a single container. As a result of the use of these components, the shelf life of the product is jeopardized every time the packaging is open and exposed to oxygen. Moreover, the production and preparation of these types of hair coloring systems require special equipment and considerable amount of time in order to make them.

Another drawback associated with the hair coloring systems of the prior art is that they are not able of selectively treating a particular kind of hair that a person has. In other words, even though the hair coloring systems of the prior art generally treats all kinds of hair, they are not capable of selectively treating one type of hair per se, for example, resistant, damaged or color treated hair.

Hence, in light of the aforementioned, there is a need for a new hair coloration or decoloration system, which by virtue of its design and components, would be able to overcome some and preferably all of the aforementioned prior art problems.

SUMMARY OF THE INVENTION

The object of the present invention is to provide a method for modifying the color of keratinous fibres which by virtue of its design and components, satisfies the above-mentioned needs.

More specifically, the object of the present invention is achieved by providing a method for permanently modifying a color of a type of keratinous fibres comprising the steps of:
a) selecting said type of keratinous fibres;
b) selecting a composition A, a composition B and a composition C according to the type of keratinous fibres selected in step a), wherein:
said composition A comprises at least a reducing agent and optionally a coloring compound,
said composition B comprises at least an alkalizing compound and having a level of basicity according to the type of keratinous fibres selected in step a), and
said composition C comprises at least an oxidizing compound;
c) providing a mixture by mixing said compositions A, B and C selected in step b);
d) applying said mixture to keratinous fibres for a suitable period of time for modifying the color of said keratinous fibres; and
e) removing said mixture from said keratinous fibres.

Another object of the present invention concerns the use of the mixture as defined above for permanently modifying the color of a type of keratinous fibres, said keratinous fibres being selected from the group consisting of hair, eyebrows and beard hair.

According to another aspect of the invention, there is provided a kit permanently modifying a color of a type of keratinous fibres comprising compositions A, B and C in separate containers wherein:
said composition A comprises at least a reducing agent and optionally a coloring compound,
said composition B comprises at least an alkalizing compound and having a level of basicity according to the type of keratinous fibres, and
said composition C comprises at least an oxidizing compound.

A further object of the present invention concerns the use of the kit as defined above for the permanent modification of the color of a type keratinous fibres, said keratinous fibres being selected from the group consisting of hair, eyebrows and beard hair.

The objects, advantages and other features of the present invention will be better understood upon reading of the following non-restrictive description of a preferred embodiment thereof, given for the purpose of exemplification only, with reference to the accompanying examples.

DETAILED DESCRIPTION OF THE INVENTION

In describing the present invention, the following terminology will be used in accordance with definitions set out below.

As used herein % or wt. % means weight % unless otherwise indicated. When used herein % refers to weight % as compared to the total weight percent of the composition that is being discussed. For example, when % is used to discuss the amount of an ingredient that is in the composition which contains the hair coloring compounds composition A, this means weight % as compared to the total weight of composition A. When weight % of the alkalizing compound in composition B is mentioned, this means the weight % as compared to the total weight of composition B. When weight % of the oxidizing compound in composition C is mentioned, this means the weight % as compared to the total weight of composition C. When the ratio of composition A to composition B and composition C is discussed this means the ratio of weight % of composition A to weight % of composition B to weight % of composition C.

By "about", it is meant that the value of weight %, pH or temperature can vary within a certain range depending on the margin of error of the method or device used to evaluate such weight %, pH or temperature.

By "keratinous fibres", it is meant hair on the head, on the face such as eyelashes, eyebrows, beard hair, and on the rest of the body such as pubic hair. Keratinous fibres preferably contemplated in the present invention are hair on the head and/or eyebrows.

The compositions and methods of the present invention are suited to be used to modify the color of different "types of hair" such as Asian, Caucasian or African hair, grey hair and previously chemically treated hair.

By "chemically treated hair" it is meant hair that has been previously treated before to be treated with the method of the present invention. For example, hair has been previously permanently waved, straightened, colored or bleached.

By "shade", it is meant the color imparted to the hair by a mixture of dyes intermediates and/or direct dyes. The different shades obtained from a combination of dyes intermediates and/or direct dyes can be described in terms of the "depth of the shade" (intensity) and the "tone" (color). The depth of a shade corresponds to the intensity of the color and can be obtained by varying the concentration of dyes intermediates and/or direct dyes, while the tone can be adjusted by the combination between primary intermediates and couplers. Different shades are designated with a letter and a number. The letter describes the tone (N for natural or neutral, R for red, A for ash, G for gold, L for no tone, etc), while the number refers to the depth of the shade, also called the level of the shade. Shade symbols and corresponding definitions are listed herein below:

| Shade symbols | Shades |
| --- | --- |
| N1 | Black |
| N2 | Very Dark Brown |
| N3 | Dark Brown |
| N4 | Medium Brown |
| N5 | Light Brown |
| N6 | Dark Blond |

-continued

| Shade symbols | Shades |
| --- | --- |
| N7 | Medium Blond |
| N8 | Light Blond |
| N9 | Very Light Blond |
| N10 | Light Light Blond |

1) Method of the Invention

According to an aspect, the present invention provides a method for permanently modifying the color of keratinous fibres. Such a method comprises a first step of providing a mixture of three compositions A, B and C. Composition A contains at least a reducing agent and optionally a coloring compound, composition B contains at least an alkalizing compound and composition C contains at least an oxidizing compound. The three compositions generate, upon mixing, controllable heat.

Then after, the method of the invention comprises a step of applying the mixture on the keratinous fibres for a suitable period of time, and a step of removing the mixture from the keratinous fibres for instance with water or a conventional shampoo or a conventional conditioning shampoo, said suitable period of time can vary in a range from 1 to 60 minutes, preferable from 15 to 45 minutes, depending on the compositions selected for preparing the mixture and of the type of hair.

In accordance with the invention, the mixture preferably contains one part of composition A with one part of composition B and two parts of compositions C. The amount of each part of each composition is selected by the user according to the quantity of keratinous fibres to treat. Compositions A has preferably about an acidic pH to about a basic pH, composition B has about a neutral pH to about a basic pH and composition C has preferably about an acidic pH to about a neutral pH. More preferably, the pH of composition A is from an acidic pH to about a neutral pH when the concentration of coloring compound is superior or equals to about 2.5 wt. % of the composition A, or the pH of composition A is ranging from a about a neutral pH to about a basic pH when the amount of coloring compounds is inferior or equals to 2.5 wt. % of the composition A.

According to a most preferred embodiment of the present invention, the pH of composition A is:
  about 6.5±0.1 when the concentration of coloring compound is superior or equals to about 2.5 wt. % of the composition A, or
  is about 10.5±0.1 when the amount of coloring compounds is inferior or equals to 2.5 wt. % of the composition A;

the pH of composition B is ranging from 10.6±0.1 to 11.3±0.1 and the pH of composition C is ranging from 3.2±0.1 to 3.4±0.1.

Therefore, the method according to the present invention may comprise at least two compositions which are acid. This advantageously ensures against premature oxidation of the compositions used in accordance with the present invention so as to provide increased stability of the same over a period of time. For example, it is well known by someone skilled in the art that coloring compounds, such as dye intermediates and direct dyes, are rapidly oxidized by the oxygen of the air. Therefore, once the container is opened, it must be used as soon as possible. According to the present invention, the coloring compounds of composition A are preferably contained in a acidic formulation (pH=6.5±0.1) when the amount of coloring compounds is superior or equal to 2.5 wt. % of the composition A, which allow the coloring compounds to be stable, even in contact with oxygen. The container of composition A once properly sealed can be shelved for a long period of time.

It is to be understood that by "a period of time", it is meant the amount of time in which compositions A, B and C according to the present invention may be shelved or kept in storage without substantial oxidizing, for instance a period up to 2 years.

It is also to be understood that the mixture of compositions A, B and C of the present invention has advantageously exothermic properties. Most of the all permanent hair coloration system presently commercialized encounter their first exothermic reaction during the product manufacturing (see Example 11), when a single composition containing both the coloring compounds, such as dye intermediates and direct dyes, and the alkalizing agent is prepared. Therefore the product will cool down until the next exothermic reaction occurs when the two parts compositions which are the alkaline color composition and the acid hydrogen peroxide solution are mixed together.

According to the present invention, the three compositions A, B and C are mixed together just prior to application on the hair in order to advantageously launched at once multiple chemical reactions. The temperature of said mixture just after its preparation, which is equals to the room temperature, increases of about +3° C. to about +20° C. By "room temperature" it is meant the temperature where compositions A, B and C have been stored and said mixture prepared.

It is well known by someone skilled in the art that the use of heat sources increases the brightness of the hair. None of the hair coloring system of the art discloses such exothermic properties and therefore, it is necessary for prior art methods to use heat generated by electrical appliances in order to obtain equivalent hair color modifications of the present invention.

It is to be understood that the exothermic properties of the mixture of the invention also allows for an improved dye penetration into the keratinous fibres, such as hair, and thus improve aesthetic properties such as conditioning and final shine.

It is worth mentioning that the exothermic properties specifically induced by the method of the present invention also allow a user to obtain a uniform and rich hair color in a reduced amount of time, comparatively to the prior art.

It is well known by someone skilled in the art that for a temperature superior to 40° C., the hydrogen peroxide will decompose and thus will lose its oxidizing property. As such a person may appreciate; the mixture of compositions A, B and C in accordance with the present invention will have a temperature that will not increase over 40° C. when said mixture is applied on keratinous fibres in accordance with the method of the present invention.

Thus, one of the advantages of using such a method for modifying the color of keratinous fibres is that it allows a user to choose his or her own personalized combination of compositions constituting such method to treat, color and/or decolor their type of keratinous fibres, for example damaged, resistant, color treated and other types of hair. Such may preferably be done by varying the alkalinity of composition B according to the present invention. In other words, depending on the type of keratinous fibres to be treated, a user may choose an appropriate composition B to modify the color of said keratinous fibres and to obtain the result they want.

This characteristic of the present invention represents an important improvement in the art of hair permanent coloration systems.

2) Kit of the Invention

According to another aspect, the present invention also relates to a kit for carrying out the hair coloring method of the invention. The kit comprises compositions A, B and C as described here above, in separate containers.

By "container", it is meant any device suitable for containing and preserving said compositions shielded from air and light and adapted to said compositions quantity and/or viscosity for convenient delivery thereof. For instance, such containers may be made of suitable materials, such as the ones encounter in the art of cosmetic products and formulation.

The kit may also preferably contain written instructions explaining how to use compositions A, B, and C of the invention.

3) Compositions A, B and C of the Invention:

What follows is a description of preferred ingredients that can be included in compositions A, B and C according to preferred embodiments of the present invention.

Composition A:

In accordance with the present invention, composition A comprises at least a reducing agent. Preferably the reducing agent consists of a thio compound. More preferably the reducing agent is selected in the group consisting of cysteamine HLC, ammonium thioglycolate and ammonium thiolactate.

The most preferred reducing agent for use in accordance with the present invention is ammonium thioglycolate.

It is further to be understood that reducing agents present in composition A of the present invention when in contact with the oxidizing agents of composition C, such as hydrogen peroxide, will produce heat induced by exothermic chemical reactions.

Reducing agent may be present in an amount ranging from about 0.01% to about 10.0%, preferably in an amount ranging from about 0.01% to about 5.0% by weight relative to the total weight of the composition A.

The amount of reducing agent in composition A varies according to the percentage of coloring compounds presents in the same composition A.

In accordance with the present invention, composition A optionally comprises coloring compounds.

It is to be understood by those skilled in the art that when composition A does not contain coloring compound, the result of the method of the present invention will be a decoloration of keratinous fibres, corresponding to a depigmentation of said keratinous fibres. It is also to be understood by those skilled in the art that when composition A contains coloring compound, the result of the method of the present invention will be a decoloration/coloration of keratinous fibres, corresponding to a depigmentation/pigmentation of said keratinous fibres.

It will be understood by those skilled in the art that concentrations of suitable coloring compounds vary depending on, for example, the intensity of the desired color.

The coloring compounds are preferably present in an amount ranging from about 0.0001% to about 10.0% by weight relative to the total weight of composition A.

More preferably, the coloring compounds are selected from the group of dyes intermediates, direct dyes and mixtures thereof. Herein after are the dyes intermediates and direct dyes preferably contemplated in accordance with the present invention:

Dye Intermediates:

Composition A of the present invention may include one or more oxidative hair coloring precursors, agents or dyes. Such oxidative hair coloring agents are used in combination with the oxidizing compound of composition C of the present invention to deliver permanent hair dye to the hair. Permanent hair dye compositions as defined herein are compositions, which once applied to the hair, are substantially resistant to washout.

The oxidation dye intermediates, or dye intermediates, used in oxidative dyes may be aromatic diamines, naphthols, phenols, aminophenols and their derivatives. These dye intermediates can be classified as primary and secondary intermediates, couplers and modifiers.

Primary intermediates are chemical compounds, which by themselves will form a dye upon oxidation. The secondary intermediates, also known as color modifiers or couplers, are used with other intermediates for specific color effects or to stabilize the color.

The dye intermediates, which are suitable for use in composition A and method, herein include aromatic diamines, naphthols, polyhydric phenols, aminophenols and derivatives of these aromatic compounds (e.g., N-substituted derivatives of the amines, and ethers of the phenols).

Dye intermediates are generally colorless molecules prior to oxidation. The oxidation dye color is generated when the primary intermediate is "activated" and subsequently joined with a secondary intermediate (coupling agent), which is also generally colorless, to form a colored, conjugated molecule. In general terms, oxidation hair dye precursors or intermediates include those monomeric materials which, on oxidation, form oligomers or polymers having extended conjugated systems of electrons in their molecular structure.

Because of the new electronic structure, the resultant oligomers and polymers exhibit a shift in their electronic spectra to the visible range and appear colored. For example, oxidation dye precursors capable of forming colored polymers include materials such as p-phenylenediamine, which has two functional groups, are capable of oxidative polymerization to yield higher molecular weight colored materials having extended conjugated electron systems.

Color modifiers (couplers), such as those detailed hereinafter, are preferably used in conjunction with the oxidation dye precursors herein and are thought to interpose themselves in the colored polymers during their formation and to cause shifts in the electronic absorption spectra thereof, thereby resulting in slight color changes. A representative list of oxidation dye precursors suitable for use herein is found in Sagarin, "Cosmetic Science and Technology", Interscience, Special Edition, Volume 2, pages 308 to 310.

It is to be understood that the oxidizing aids of the present invention are suitable for use (in combination with a source of peroxide as detailed herein) with all manner of oxidation dye precursors and color modifiers and that the precursors detailed below are only by way of example and are not intended to limit the compositions and processes herein.

The typical aromatic diamines, polyhydric phenols, aminophenols, and derivatives thereof, described above as primary dye precursors can also have additional substituents on the aromatic ring, e.g. halogen, alkyl, alkyl substituted additional substituents on the amino nitrogen and on the phenolic oxygen, e.g. substituted and unsubstituted alkyl and aryl groups.

Composition A of the present invention may, in addition to the essential oxidative hair-coloring agents, optionally include non-oxidative and other dye materials. Optional non-oxidative and other dyes suitable for use in the hair coloring compositions and processes according to the present invention include semi-permanent, temporary and other dyes. Non-oxidative dyes as defined herein include the so-called "direct dyes", metallic dyes, metal chelate dyes, fibre reactive dyes and other synthetic and natural dyes as detailed in "Chemical and Physical Behaviour of Human Hair", 3rd Edn. by Clarence Robbins (pp 250-259); "The Chemistry and Manufacture of Cosmetics". Volume IV. 2nd Edn. Maison G. De dyes. Various types of non-oxidative dyes are detailed in: 'Navarre at chapter 45 by G. S. Kass (pp 841-920); 'cosmetics: Science and Technology' 2nd Edn, Vol. 11 Balsam Sagarin, Chapter 23 by F. E. Wall (pp 279-343); 'The Science of Hair Care' edited by C. Zviak, Chapter 7 (pp 235-261) and 'Hair Dyes', J. C. Johnson, Noyes Data Corp., Park Ridge, U.S.A. (1973), (pp 3-91 and 113-139).

Specific hair dyes which may be included in the compositions as the primary intermediate includes: 3-methyl-p-aminophenol; 2,3-dimethyl-p-aminophenol; p-phenylenediamine, p-toluenediamine; 2-chloro-p-phenylenediamine; N-phenyl-p-phenylenediamine; N-2-methoxyethyl-p-phenylene-diamine; N,N-bis-(hydroxyethyl)-p-phenylenediamine; 2-hydroxymethyl-p-phenylenediamine; 2-hydroxyethyl-p-phenylenediamine; 4,4'-diaminodiphenylamine; 2,6-dimethyl-p-phenylenediamine; 2-isopropyl-p-phenylenediamine; N-(2-hydroxypropyl)-p-phenylenediamine; 2-propyl-p-phenylene-diamine; 1,3-di-(p-N,N-bis-(2-hydroxyethyl)-aminoanilino)-2-propanol; 2-methyl-4-dimethylaminoaniline; p-aminophenol; p-methylaminophenol; 2-hydroxymethyl-p-aminophenol; 2-methyl-p-aminophenol; 2-(2-hydroxyethylaminomethyl)-p-aminophenol; 2-methoxymethyl-paminophenol; and 5-aminosalicylic acid; catechol; pyrogallol; o-aminophenol; 2,4-diaminophenol; 2,4,5-trihydroxytoluene; 1,2,4-trihydroxy-benzene; 2-ethylamino-p-cresol; 2,3-dihydroxpaphthalene; 5-methyl-o-aminophenol; 6-methyl-o-aminophenol; 2-amino-5-acetaminophenol; 2,5-diaminotoluene; 2-dimethylamino-5-aminopyridine; tetraminopyrimidine; 4,5-diamino-1-methylpyrazole; 4,5-diamino-1-hydroxyethylpyrazole, 6-methoxy-8-aminoquinoline; 2,6-dihydroxy-4-methylpyridine; 5-hydroxy-1,4-benzodioxane; 3,4-methylenedioxyphenol; 4-hydroxyethylamino-1,2-methylenedioxybenzene; 5-chloro-2,3-dihydroxypyridine; 2-hydroxyethylamino-6-methoxy-3-aminopyridine; 3,4-methylenedioxyaniline; 7-hydroxy-indole; 5-hydroxyindole; 2-bromo-4,5-methylenedioxyphenol; 3-amino-2-methylamino-6-methoxypyridine; 2-amino-3-hydroxypyridine; 4-hydroxy-2,5,6-triaminopyrimidine, 5-hydroxyindoline, 7-hydroxyindoline or combinations thereof.

Preferred primary intermediates for use in the invention include: p-phenylenediamine; p-aminophenol; N,N-bis(2-hydroxyethyl)-p-phenylenediamine; 2,5-toluenediamine; 2-methyl-p-aminophenol; 3-methyl-p-aminophenol; 2,3-dimethylp-aminophenol; p-methylaminophenol; 4,5,-diamino-1-hydroxyethylpyrazole; 2,4,5,6-tetra-aminopyrimidine; 4-hydroxy-2,5,6-triaminopyrimidine; o-aminophenol; N-phenyl-p-phenylenediamine and mixtures thereof.

The most preferred primary intermediates are p-phenylenediamine; p-aminophenol; o-aminophenol; N,N-bis (hydroxyethyl)-p-phenylenediamine; 2,5-toluenediamine; N-phenyl-p-phenylenediamine and mixtures thereof.

The coupler (or secondary intermediate) is utilized to expand the color range by copolymerization with the primary intermediate. These materials can also accelerate color formation.

Specific hair dye intermediates that can be used as couplers in the present invention include but not limited to 4-amino-m-cresol, 2-amino-4-hydroxy-ethylaminoanisole, 4-amino-2-hydroxy-toluene, 4-amino-3-nitrophenol, m-aminophenol, 2-chloro-p-phenylene-diamine, 4-chlororesorcinol, 2,4-diaminophenoxy-ethanol, 2-methylresorcinol, 1-naphthol, 3-nitro-p-hydroxyethyl-aminophenol, 4-nitro-o-phenylene-diamine, 2-nitro-p-phenylene-diamine, phenyl-methylpyrazolone, m-phenylenediamine, resorcinol, 2-methyl-5-hydroxyethyl-aminophenol and mixtures thereof.

It should be understood that the descriptions of primary intermediates and couplers given above are meant to implicitly include the salt forms of those dye molecules that form stable salts. For example, the hydrochloride or sulfate salts in the case of amines, and the alkali metal salts in the case of phenols.

Direct Dyes

Direct dyes are colored compounds that can be used to modify the color of a substrate by dispersion. Direct dyes are used along with the dyes intermediates to add vibrancy to the tone which is not otherwise available if the composition only contains oxidation dye intermediates.

The dye composition disclosed herein may also comprise at least one direct dye that may be chosen, for example, from nitrobenzene dyes, cationic direct dyes, azo direct dyes and methine direct dyes.

According to a preferred embodiment of the present invention, the direct dyes can be chosen in a group of compounds containing Basic Blue #3, External D & C Violet #2, Basic Green #4, Basic Orange #1, Basic Red #22, Red #2, Basic Red #46, Basic Violet #13, Basic Violet #1, Basic Yellow #11, Basic Yellow #28, Basic Brown #16, Basic Brown #17, Basic Blue #99, and mixtures thereof.

According to a preferred embodiment of the present invention, composition A optionally contains an amount of alkalizing compound. Preferably, the alkalizing compound is selected in the group consisting of ammonium hydroxide, monoisopropanolamine, monoethanolamine (MEA), aminoethylpropanol, potassium hydroxide, sodium hydroxide and mixtures thereof. The amount of alkalizing compound that may be used in composition A of the present invention is preferably ranging from about 1.0% to about 20.0% of composition A. It is to be understood that the pH of composition A will depend on the amount of alkalizing compound used in said composition A. Preferably, composition A of the invention has a pH in the range of from about 1.0 to about 14.0, preferably from about 6.0 to about 11.0.

According to a more preferred embodiment of the invention, the alkalizing compound used in the present invention is monoethanolamine.

It is to be understood that composition A is either acid or alkaline depending on the concentration of coloring compounds.

It is well known by someone skilled in the Art that darker shades, due to a high concentration of dyes, are rapidly oxidized by the oxygen of the air, therefore, an acid environment is preferable which allows longer stability of Composition A.

Composition A, which contains an amount of coloring compounds such as dyes intermediates and/or direct dyes superior or equal to about 2.5%, is preferably acid with a most preferable pH of about 6.5.

Lighter shades which contain lower concentration of coloring compounds are directly related to the lightning of keratinous fibres, therefore, the alkalizing agent is added to increase the lightning power of the product. Composition A, which contains an amount of coloring compounds inferiors to about 2.5%, also contains an alkalizing compound. Therefore, the amount of alkalizing compound is preferably ranging from 1.0 to 7.0 wt. % of composition A, and thus the pH of composition A is preferably basic, and more preferably the pH of composition A is about 10.5.

Unlike the basic pH used in hair coloring compositions present in the prior art, it is to be understood herein that the use of an acidic pH in compositions containing high concentration of dyes chemically stabilizes the coloring compounds, such as dyes intermediates and direct dyes, before and even after the opening of the container containing composition A and contact of said composition A with the oxygen of the atmosphere.

Optionally, the pH of composition A may be adjusted to the preferred pH described herein above by using an acidifying solution. It will be understood that the amount of acidifying solution added in composition A will depend on the nature of the acidifying solution itself and the starting pH of composition A.

Specific acidifying solutions which may be used to adjust the pH of composition A of the present invention preferably contain organic acids. A non-exclusive list of examples of organic acids which can be used as the proton donating agent is adipic acid, tartaric acid, citric acid, maleic acid, malic acid, succinic acid, glycolic acid, glutaric acid, benzoic acid, malonic acid, salicylic acid, gluconic acid, polyacrylic acid, their salts, and mixtures thereof.

The most preferred acidifying solution for use in accordance with the present invention is citric acid solution containing about 30% of citric acid.

Optionally, composition A of the present invention will also contain the compounds selected in the group consisting of solvents, thickeners and others optional ingredients.

More preferably, the thickeners used in composition A of the invention may be long chain fatty alcohols having from about 11 to about 18 carbon atoms in the long fatty chain, used alone, or in admixture with each other. When included in the compositions, the fatty alcohols are preferably present at from about 0.5% to about 20.0% by weight percent of composition A.

Other thickeners suitable for use in the compositions A of the present invention are preferably selected from the group consisting of Xanthan gum; Hydrophobically-modified ethoxylated Urethane (HEUR) such as PEG-150/Stearyl alcohol copolymer or Aculyn® 46 (from Rohm and Haas, Philadelphia, Pa., USA); alkoxylated alcohols such as Ceteareth-20; long chain fatty alcohols such as cetyl alcohol, oleyl alcohol, cetearyl alcohol, stearyl alcohol; Simulgel® NS (or hydroxyethylacrylate/sodium acryloyldimethyl taurate copolymer (and) squalane (and) polysorbate 60), (from Seppic), sodium chloride and other synthetic thickeners such as Carbopol®, Aculyn®, Structure®, and Acrosyl and mixtures thereof. Hydroxyalkylcellulose, such as hydromethylcellulose and hydroethylcellulose, are also suitable thickeners for use in compositions A of the present invention.

Water, and preferably deionised water, is the preferred principal solvent, carrier or diluent for compositions A according to the present invention. Water may be present in an amount ranging from about 15% to about 99% by weight relative to the total weight of composition A.

As such, composition A according to the present invention may include one or more solvents as additional solvent, carrier or diluent materials. Generally, the solvent is preferably selected to be miscible with water, to be innocuous to the skin and to dissolve dyes intermediates or direct dyes which would not be perfectly miscible in water. Solvents suitable for use in accordance with the present invention are included but not limited to $C_1$-$C_{20}$ mono- or polyhydric alcohols and their ethers, glycerine, with monohydric and dihydric alcohols and their ethers. In these compounds, alcohols preferably contain 2 to 10 carbon atoms. Thus, a particularly preferred group includes ethanol, isopropanol, propylene glycol, hexylene glycol, ethoxydiglycol and mixtures thereof, and a more preferable group includes propylene glycol, ethoxydiglycol and mixtures thereof.

Propylene glycol may be present in an amount ranging from about 0.1% to about 20%, preferably in an amount ranging from about 5% to about 15% by weight relative to the total weight of composition A. Ethoxydiglycol may be present in an amount ranging from about 0.1% to about 30.0%, preferably in an amount ranging from 9.0% to 25.0% by weight relative to the total weight of composition A.

Optionally, composition A of the present invention preferably comprise a wide range of optional ingredients listed in the group constituting of anticaking agents, antioxidants, binders, biological additives, bulking agents, chelating agents, chemical additives, colorants, cosmetic astringents, cosmetic biocides, denaturants, drug astringents, surfactants, emulsifiers, film formers, fragrance components, humectants, opacifying agents, plasticizers, preservatives, propellants, foam boosters, hydrotropes, solubilizing agents, suspending agents (non surfactant), sunscreen agents, ultraviolet light absorbers, and viscosity increasing agents (aqueous and non aqueous). Examples of other functional classes of materials useful herein that are well known to one of ordinary skill in the art include solubilizing agents, sequestrants, amino acids, hydrolysed proteins and the like.

Composition B:

In accordance with the present invention, composition B comprises at least an alkalizing compound which aids the swelling of the keratinous fibres and contributes to the exothermic reaction occurring after the mixing of the three compositions A, B and C. Consequently, the alkalinity improves the ability of the keratinous fibres to absorb moisture and thus to accept the coloring compounds more readily.

According to a preferred embodiment of the invention, the alkalizing compound is selected in the group consisting of ammonium hydroxide, monoisopropanolamine, monoethanolamine (MEA), aminoethylpropanol, potassium hydroxide, sodium hydroxide and mixtures thereof. Preferably, the quantity of alkalizing compound that may be used in composition B of the present invention is ranging from about 1.0% to about 10.0%. It is to be understood that the pH of composition B will depend on the amount of alkalizing compound used in said composition B. Preferably, composition B of the invention has a pH in the range of from about 7.0 to about 14.0, preferably from about 10.0 to about 12.0.

According to a more preferred embodiment of the invention, the alkalizing compound used in the present invention is monoethanolamine.

Composition B may be provided with at least three different levels of basicity which are mild, regular or strong.

For instance, a mild level of basicity is obtained when about 5.0% of monoethanolamine are used by weight of composition B, which substantially corresponds to a pH of about 10.9 for composition B; a regular level of basicity is obtained when about 6.0% of monoethanolamine are used by weight of composition B, which substantially corresponds to a pH of about 11.1 for composition B; a strong level of basicity is obtained when about 7.0% of monoethanolamine are used by weight of composition B, which substantially corresponds to a pH of about 11.3 for composition B.

Therefore, the user has the possibility of choosing suitable compositions B depending on the type of keratinous fibres to be treated and the expected color modification of the keratinous fibres.

Optionally, composition B will also contains compounds selected in the group constituting of solvents, thickeners, optional ingredients and mixtures thereof. Solvents, thickeners, optional ingredients and amounts thereof may be the same as defined herein above for composition A.

Composition C:

In accordance with the present invention, composition C comprises at least an oxidizing compound.

According to a preferred embodiment of the invention, the oxidizing compounds are generally inorganic peroxygen materials capable of yielding peroxide in an aqueous solution. Inorganic peroxygen oxidizing agents are well known in the art and include hydrogen peroxide, inorganic alkali metal peroxides such as sodium periodate, sodium perbromate and sodium peroxide, and inorganic perhydrate salt oxidizing compounds, such as the alkali metal salts of perborates, percarbonates, perphosphates, persilicates, persulphates and the like. These inorganic perhydrate salts may be incorporated as monohydrates, tetrahydrates etc. Also useful are melamine peroxide, sodium perborate, and sodium percarbonate. Mixtures of two or more of such inorganic peroxygen oxidizing agents can be used. For all of these compounds, the active material is active hydrogen peroxide. One skilled in the art would recognize how much active hydrogen peroxide is desired in composition C relatively to the amount of coloring compounds that are being formulated in composition A and the nature of the hair of the user. Therefore, one skilled in the art would be able to calculate how much of a peroxide compound to use in accordance with the present invention.

According to a more preferred embodiment of the present invention, the oxidizing compound used in composition C is hydrogen peroxide ($H_2O_2$).

As it is well known by someone skilled in the art, the unit for measuring the concentration of hydrogen peroxide is the Volume (Vol.). The volume of a hydrogen peroxide solution is the number of liters of oxygen in its gaseous form released by the decomposition taking place in a liter of that particular hydrogen peroxide solution.

Preferably, the different volumes of $H_2O_2$ being part of composition C of the present invention are listed in the following table 1:

| Volume | Quantity of $H_2O_2$ 50% solution (wt. %) | Final quantity of $H_2O_2$ in Compound C (wt %) |
|---|---|---|
| 5 Vol. | 2.85 | 1.43 |
| 10 Vol. | 5.70 | 2.85 |
| 20 Vol. | 11.40 | 5.70 |
| 30 Vol. | 17.10 | 8.55 |
| 40 Vol. | 22.80 | 11.40 |

According to a preferred embodiment of the invention, the pH of composition C is in the range of from about 1.0 or to about 7.0, preferably from about 2.0 to about 4.0; and more preferably ranging from about 3.2 to about 3.4.

Optionally, composition C will also contains compounds selected in the group constituting of solvents, thickeners, optional ingredients and mixtures thereof. Solvents, thickeners, optional ingredients and amounts thereof may be the same as defined herein above for composition A.

It is to be understood that, regarding only composition C, the presence of an oxidizing compound, such as hydrogen peroxide, makes some of the here before mentioned thickeners, solvents, alkalizing agents and reducing, not suitable for the preparation of composition C. For example, it is well known by someone skilled in the art that the viscosity of an aqueous solution containing hydroxyalkylcellulose as thickener, strongly decreased because of an important hydrolysis due to a pH of composition C inferiors to about 4.0 and the elevated concentration of $H_2O_2$. It is also well known by someone skilled in the art that propylene glycol and ethoxidiglycol oxidize in the presence of $H_2O_2$.

EXAMPLES

The following examples below, which were made, are shown as illustrations only and are not intended to limit the scope of the invention. The below compositions may be made by methods which are known in the art.

Example 1

Preferred Ingredients Constituting Composition A

This example, resumed in the following table 2, shows ingredients of composition A according to preferred embodiments of the present invention.

TABLE 2

| Functions | Ingredients | Quantities (wt. %) |
|---|---|---|
| Solvent | Deionised Water | Balance* |
| Solvent | Propylene Glycol | 5.55 |
| Solvent | Ethoxydiglycol | 18.0 |
| Antioxidant | Sodium Sulfite (Inorganic Salt) | 1.0 |
| Antioxidant | Sodium Isoascorbate (organic Salt) | 1.0 |
| Coloring compounds | Dyes Intermediates / Direct Dyes* | 0 to 10.0* |
| Reducing Agent | Ammonium Thioglycolate | 0.01 to 5.0* |
| Alkalizing compound | Monoethanolamine | 0 to 7.0* |
| Chelating Agent | Trisodium HEDTA | 0.35 |
| Thickener | Stearyl Alcohol (Fatty Alcohol) | 10.0 |
| Thickener | Cetyl Alcohol (Fatty Alcohol) | 10.0 |
| Surfactant | Oleic Acid | 4.0 |
| Nonionic Surfactant | Polysorbate 20 | 1.5 |
| Colorant | Titanium Dioxide | 2.0 |
| Preservative | DMDM Hydantoin | 0.3 |
| Fragrance | Fragrance | 0.5 |
| | Total weight. % | 100 |

*See Examples 5 to 9 for specific quantities.

It is to be understood that the nature and amount of the coloring compounds, such as dye intermediates and/or direct dyes, are measured according to the tone and depth of the shade.

It is also to be understood that the amount of reducing agent, such as ammonium thioglycolate, is measured according to the concentration of coloring compounds, such as dye intermediates and/or direct dyes, contained in composition A (depth of the shade). (See Example 5 to 9)

According to another embodiment of the present invention, the pH of composition A can be adjusted to 6.5 using an acidifier, such as citric acid 30% solution.

Example 2

Preferred Ingredients Constituting Composition B

This example resumed in the following table 3 shows ingredients of composition B according to preferred embodiments of the present invention.

TABLE 3

| Function | Ingredients | Quantity (wt. %) |
|---|---|---|
| Solvent | Deionised water | balance |
| Thickener/Conditioner/Film former | Hydroxyethylcellulose | 0.65 |
| Colorant | Titanium Dioxide | 0.30 |
| Scalp Protector/Conditioner | Monoi Oil (Natural extract) | 2.0 |
| Humectant | Glycerine | 1.0 |
| Conditioner | Olealkonium Chloride | 1.5 |
| Anti-Static/ Conditioner | Benzalkonium Chloride | 0.5 |
| Surfactant | Polysorbate 20 | 1.5 |
| Preservative | DMDM Hydantoin | 0.4 |
| Alkalizing Agent | Monoethanolamine | 5.0, 6.0 or 7.0* |
| Fragrance | Fragrance | 0.5 |
| | Total weight. % | 100 |

*See Example 4 to 9 for specific quantity.

It is to be understood that the amount of alkalizing compound, such as monoethanolamine, is selected according to the nature of the user hair to color and his/her choice for a new hair color (See Examples 4 to 9).

As already mentioned, according to preferred embodiment of the present invention, the alkalizing agent is monoethanolamine and according to the amounts used in composition B, three different level of basicity are defined, such as:

i) Mild Level of Basicity (Corresponding to 5.0 Wt. % of Monoethanolamine in Composition B):

This mild level of basicity can be used for treating hair that had been previously chemically treated such as chemically straightened hair, permanent waves hair, color-treated hair or bleached hair. Such hair is porous and absorbs color quickly.

ii) Regular Level of Basicity (Corresponding to 6.0 Wt. % of Monoethanolamine in Composition B):

This regular level of basicity can be used for 100% grey coverage and lightening of natural pigment up to 3 levels, for example from N4 (Medium Brown shade) to N7 (Medium Blond shade). Tests involved the use of hair swatches such as natural medium brown, natural light blond, 50% grey hair and bleached hair. However, final formula adjustments were done according to tests on human heads.

iii) Strong Level of Basicity (Corresponding to 7.0 Wt. % of Monoethanolamine in Composition B):

This strong level of basicity can be used for lightening natural pigment up to 5 levels, for example from N4 (Medium Brown shade) to N9 (Very Light Blond shade) along with dyeing process and give extra coverage for very resistant grey hair.

Compositions B were tested on hair swatches and human heads.

Example 3

Preferred Ingredients Constituting Composition C

This example, resumes in the following table 4, shows ingredients of composition C according to preferred embodiments of the present invention.

TABLE 4

| Function | Ingredients | Quantity (wt. %) |
|---|---|---|
| Solvent | Deionised Water | Balance |
| Oxidizing compound | Hydrogen Peroxyde | 2.85 to 22.80* |
| | (50 wt. % solution) | |
| Stabilizer | Sodium Stannate | 0.01 |
| Surfactant | Sodium Lauryl Sulfate | 1.00 |
| Opacifier | Cetyl Alcohol | 1.10 |
| Thickener | Stearyl Alcohol | 1.00 |
| Emulsifier | Ceteareth 5 | 0.85 |
| | Total weight | 100 |

*See Examples 5 to 9

It is to be understood that the amount of oxidizing compound, such as hydrogen peroxide, is selected according to the nature of the user hair to color and his/her choice for a new hair color (See Examples 5 to 9).

The resulting pH of composition C is ranging from 3.2±0.1 to 3.4±0.1. As already mentioned herein above, the preferred oxidizing compound is hydrogen peroxide. It is known in the art that hydrogen peroxide is stable in the pH range from 2.0 to 4.0. The pH of composition C of the present invention is therefore suitable for the stability of hydrogen peroxide.

Example 4

A Preferred Method for Using Compositions A, B and C for Changing Hair Color

This example shows a preferred method for changing color of keratinous fibres, such as hair, according to preferred embodiments of the present invention.

According to his/her hair nature, original color and expected final color, the user selects suitable compositions A, B and C as preferably described in Examples 1 to 3.

In a preferred non-metallic container, compositions A, B and C mixed together with a ratio of about 1:1:2 in weight % of the mixture and then applied on hair and/or eyebrows. The amount of each compositions used for preparing the mixture depends on the amount of keratinous fibres to treat. The mixture is maintained in the hair and/or eyebrows for a suitable period of time from 15 to 45 minutes.

Example 5

A Kit for Changing the Color of Virgin Natural Dark Brown Hair (N3) Containing 50% of Grey Hair to Natural Light Brown (N5)

This example shows a kit for modifying the color of virgin natural Dark Brown hair (N3) including about 50% of grey hair to Natural Light Brown (N5) according to preferred embodiments of the present invention.

To reach the desired objective, the selected kit contains:
a) Composition A comprising the basic ingredients listed in Example 1 with specifically 2.0 wt. % of ammonium thioglycolate and 3.4282 wt. % of dyes. To obtain Natural light brown (N5), the selected dyes are:

TABLE 5

| Dyes | Quantity (wt. %) |
|---|---|
| p-Phenylenediamine | 1.4787 |
| m-Aminophenol | 0.0729 |
| Resorcinol | 0.9322 |
| p-Aminophenol | 0.4095 |

TABLE 5-continued

| Dyes | Quantity (wt. %) |
|---|---|
| 2-Methylresorcinol | 0.1782 |
| 4-Chlororesorcinol | 0.3567 |

The resulting pH of compound A is about 6.5±0.1.
b) In this particular example, composition B contains the basic ingredients listed in Example 2, with specifically 6.0 wt. % of Monoethanolamine (which correspond to a Regular level of basicity) to cover resistant grey hair. The resulting pH of compound B is 11.1±0.1.
c) In this particular example, only two levels of keratin lightning is required (from N3 to N5). Therefore, composition C comprises the basic ingredients listed in Example 3, and specifically requires 11.40 wt. % of hydrogen peroxide 50 wt. % solution (20 Volume). The resulting pH of compound C is from 3.2±0.1 to 3.4±0.1.

In this particular case, the mixture of compositions A, B and C is prepared as disclosed in Example 4 and applied on hair and/or eyebrows for 45±5 minutes. The exothermic reaction occurs when the three compositions are mixed together. The heat generated lasts until processing time is completed. In this particular example, the temperature increased by (8±1)° C. from 23° C. (room temperature) to 31°.

Example 6

A Kit for Changing Color of Permanent Waved Natural Dark Blond Hair (N6), Free of Grey Hair, to Violet Red (R3)

This example shows a kit for modifying the color of permanent waved natural Dark Blond hair (N6), free of grey hair, to Violet Red (R3), according to preferred embodiments of the present invention.

To reach the desired objective, the selected kit contains:
a) Composition A containing the ingredients listed in Example 1, with specifically 2.0 wt. % of ammonium thioglycolate and 2.9584 wt. % of dyes. To obtain Violet Red (R3) colored hair, the selected dyes are:

TABLE 6

| Dyes | Quantity (wt. %) |
|---|---|
| p-Phenylenediamine | 1.1387 |
| 4-Amino-2-hydroxytoluene | 1.2967 |
| p-Aminophenol | 0.2070 |
| 2-Methyl-5-hydroxyethylaminophenol | 0.3160 |

The resulting pH of compound A is about 6.5±0.1.
b) In this particular example, composition B contains the ingredients listed in Example 2, with specifically 5.0 wt. % of Monoethanolamine (Mild level of basicity) to cover chemically treated hair (permanent waved hair). The resulting pH of compound B is 10.9±0.1.
c) In this particular example, no keratin lightning is required (N-6 to R-3). Therefore, composition C comprises the different ingredients listed in Example 3, and specifically requires 5.70 wt. % of hydrogen peroxide 50 wt. % solution (10 Volume). The resulting pH of compound C is from 3.2±0.1 to 3.4±0.1.

In this particular example the mixture of compositions A, B and C is applied on hair and/or eyebrows for 25±5 minutes. The exothermic reaction occurs when the three compositions are mixed together. The heat generated lasts until processing time is completed. In this particular example, the temperature increased by (7±1)° C. from 26° C. (room temperature) to 33° C.

Example 7

A Kit for Changing the Color of Virgin Natural Dark Blond Hair (N6), Free of Grey Hair, to Light, Light Ash Blond (A10)

This example shows a kit for modifying the color of virgin natural Dark Blond hair (N6), free of grey hair, to Light, Light Ash Blond (A10), according to preferred embodiments of the present invention.

To reach the desired objective, the selected kit contains:
a) Composition A containing the ingredients listed in Example 1, with specifically 5.0 wt. % of ammonium thioglycolate, 0.5050 wt. % of dyes and 7% of monoethanolamine to obtain Light, Light Ash Blond hair color (A10), the selected dyes are:

TABLE 7

| Dyes | Quantity (wt. %) |
|---|---|
| p-Phenylenediamine | 0.0905 |
| 2-Amino-4-hydroxyethylamino anisol sulphate | 0.0092 |
| 4-Amino-m-cresol | 0.0137 |
| Resorcinol | 0.0655 |
| p-Aminophenol | 0.0032 |
| 4-Chlororesorcinol | 0.0032 |
| 1-Naphtol | 0.0037 |
| Eternal D & C violet #2 | 0.3160 |

The resulting pH of compound A is about 10.5±0.1.
b) In this particular example, composition B comprises the ingredients listed in Example 2, with specifically 7.0 wt. % of Monoethanolamine (Strong level of basicity) for lightning natural Dark Blond (N6) hair color. The resulting pH of compound B is 11.3±0.1.
c) In this particular example, four levels of keratin lightning is required (N-6 to A-10). Therefore, composition C comprises the ingredients listed in Example 3 and specifically required 17.10 wt. % of hydrogen peroxide 50 wt. % solution (30 Volume). The resulting pH of compound C is from 3.2±0.1 to 3.4±0.1.

The mixture of compositions A, B and C is prepared as disclosed in Example 4 and applied on hair and/or eyebrows for 35±5 minutes. The exothermic reaction occurs when the three compositions are mixed together. The heat generated lasts until processing time is completed. In this particular example, the temperature increased by (8±1)° C. from 23° C. (room temperature) to 31° C.

Example 8

A Kit for Changing the Color of Virgin Natural Medium Brown Hair (N4), Free of Grey Hair, to Light Blond (N8)

This example shows a kit for changing the color of virgin natural Medium Brown hair (N4), free of grey hair, to Light Blond (N8), according to preferred embodiments of the present invention.

To reach the desired objective, the selected kit contains:
a) Composition A containing the ingredients listed in Example 1, with specifically 5.0 wt. % of ammonium thioglycolate, 1.0150 wt. % of dyes and 7% of monoethanolamine to obtain hair with Light Blond color (N8), the selected dyes are:

TABLE 8

| Dyes | Quantity (wt. %) |
|---|---|
| p-Phenylenediamine | 0.2546 |
| m-Aminophenol | 0.0029 |
| Resorcinol | 0.2341 |
| 2-Methylresorcinol | 0.0077 |
| 4-Chlororesorcinol | 0.0157 |
| o-Aminophenol | 0.5000 |

The resulting pH of compound A is about 10.5±0.1.

b) Composition B comprising the ingredients listed in Example 2, with specifically 6.0 wt. % of Monoethanolamine (Regular level of basicity) for lightning natural Medium Brown (N4) hair color. The resulting pH of compound B is 11.1±0.1.

c) In this particular example, four levels of keratin lightning is required (N-4 to N-8). Therefore, composition C comprises the ingredients listed in Example 3 and specifically requires 22.80 wt. % of hydrogen peroxide 50 wt. % solution (40 Volume). The resulting pH of compound C is from 3.2±0.1 to 3.4±0.1.

The mixture of compositions A, B and C is applied on hair and/or eyebrows for 35±5 minutes. The exothermic reaction occurs when the three compositions are mixed together. The heat generated lasts until processing time is completed. In this particular example, the temperature increased by 13±1° C. from 24° C. (room temperature) to 37°.

Example 9

A Kit for the Decoloration of Virgin Natural Medium Brown Hair (N4), Free of Grey Hair, to Very Light Streaks (L9)

This example shows a kit for lightening virgin natural Medium Brown hair (N4), free of grey hair. This application lightens up to five levels to Very Light Blond (L9), according to preferred embodiments of the present invention.

To reach the desired objective, the selected kit contains:

a) Composition A containing the ingredients listed in Example 1, with specifically 5.0 wt. % of ammonium thioglycolate and 7.0% of monoethanolamine. In that particular application, composition A does not contain dyes. The resulting pH of compound A is about 10.5±0.1.

b) Composition B comprising the ingredients listed in Example 2, with specifically 7.0 wt. % of monoethanolamine (Strong level of basicity) for lightning natural Medium Brown (N4) hair color. The resulting pH of compound B is 11.3±0.1.

c) In this particular example, five levels of keratin lightning is required (N-4 to Level 9). Therefore, composition C comprises the ingredients listed in Example 3 and specifically requires 22.80 wt. % of hydrogen peroxide 50 wt. % solution (40 Volume). The resulting pH of compound C is from 3.2±0.1 to 3.4±0.1.

The mixture of compositions A, B and C is prepared as disclosed in Example 4 and is prepared as disclosed in Example 4 and applied on hair and/or eyebrows for 35±5 minutes. The exothermic reaction occurs when the three compositions are mixed together. The heat generated lasts until processing time is completed. In this particular example, the temperature increased by 13±1° C. from 25° C. (room temperature) to 38° C.

Example 10

Influence of the Reducing Agent on the Increase of Temperature

This example shows how the presence of the reducing agent in composition A influences the increase of the temperature, according to preferred embodiments of the present invention.

An exothermic reaction occurs between the reducing agent present in composition A, such as ammonium thioglycolate, the alkalizing compound present in composition B, such as the monoethanolamine, and the oxidizing compound present in composition C, such as hydrogen peroxide. All results are based on a starting room temperature of 24° C.

Three different dyes loadings (weight) corresponding to three different desired shades have been tested (See Table 9).

TABLE 9

| Dyes intermediates loading (wt. %) | Ammonium Thioglycolate (wt. %) | Hydrogen Peroxide (wt. %) | Optimal temperature (° C. ± 1° C.) | Range of temperature (° C. ± 1° C.) |
|---|---|---|---|---|
| 8.0 (Black Shade) | 0 | 1.5 | 27 | +3 |
| | 0.8 | 1.5 | 28 | +4 |
| 4.5 (Brown shade) | 0 | 1.5 | 27 | +3 |
| | 2.0 | 1.5 | 30 | +6 |
| 1.03 (Light blond shade) | 0 | 6 | 28 | +4 |
| | 5.0 | 6 | 35 | +13 |
| 0.24 (Light, light blond shade) | 0 | 12 | 29 | +5 |
| | 5.0 | 12 | 37 | +13 |

It is to be understood that in the absence of ammonium thioglycolate, the range of temperature varies only from +1° C. to +6° C., where in the presence of ammonium thioglycolate; the range of temperature varies from +4° C. to +13° C. In fact, the range variation depends on the percentage of ammonium thioglycolate contained in the shade formulation, monoethanolamine concentration and hydrogen peroxide concentration. This range includes all shades containing a dye concentration between 0.24% and 8.0%.

It is also to be understood that the percentage of ammonium thioglycolate is calculated taking in consideration the concentration of monoethanolamine used in composition B and the concentration of hydrogen peroxide used in composition C. Therefore, under normal conditions and proper use, no over-heating of the mixture occurs. It is due to this safety measure that temperature varies. Indeed, when concentration of hydrogen peroxide decreases so will the temperature.

Example 11

Comparison Between the Kit of the Present Invention with Those of the Prior Art

This example shows some temperature increases comparison between a kit according to preferred embodiments of the present invention with products from the prior art.

It is important to mention that for each comparison, several tests were performed by using the same level shade and same quantity of oxidizing compound, such as 6 wt. % hydrogen peroxide.

TABLE 10

| Shade Tone and Level | Companies | | | | |
|---|---|---|---|---|---|
| | Vernico | Voilà | Framcolor | Swarzkopf | L'Oréal |
| Medium Reddish Brown (4.66) | 29° C. | 21.5° C. | N/A | N/A | N/A |
| Natural Dark Brown (N-3) | 29° C. | N/A | 22.5° C. | N/A | N/A |
| Medium Ash Brown (A-4) | 29° C. | N/A | N/A | 21.5° C. | N/A |
| Tropical Red (4.65) | 29° C. | N/A | N/A | N/A | 22° C. |

Four distinct shades from four different companies were color matched and tested for degree of exothermic reaction. Products' temperature before mixing with oxidizer is 21° C.

The invention claimed is:

1. A method for personalizing the permanent modification of a color of a type of keratinous fibres of a person comprising the steps of:
   a) selecting a color modification desired by the person;
   b) selecting a composition A according to the color modification selected in step a), wherein said composition A comprises from about 0.01% to about 10% of a reducing agent and from 0% to about 10% of a coloring compound, by weight of composition A;
   c) determining a type of keratinous fibres to be colored;
   d) selecting a composition B comprising an alkalizing compound, wherein composition B has a level of basicity selected according to the type of keratinous fibres selected in step c) and the type of color modification selected in step a);
   e) selecting a composition C comprising from about 1.5% to about 12% of an oxidizing compound by weight of composition C, wherein the amount of oxidizing compound is selected according to the type of color modification selected in step a) and the type of keratinous fibres selected in step c);
   f) mixing said compositions A, B and C to obtain a mixture, said mixture providing heat generated by an exothermic chemical reaction which provides a temperature that increases progressively from room temperature (RT) to a temperature ranging from about RT+3° C. to about RT+20° C.;
   g) applying said mixture to keratinous fibres immediately after the mixing of compositions A, B and C, for a suitable period of time for obtaining the color modification selected in step a;
   h) removing said mixture from said keratinous fibres.

2. The method of claim 1, wherein said reducing agent consists in a thio compound.

3. The method of claim 1, wherein said reducing agent is selected from the group consisting of cysteamine HLC, ammonium thioglycolate and ammonium thiolactate.

4. The method of claim 1, wherein said coloring compound is selected from the group consisting of dye intermediates, direct dyes and mixtures thereof.

5. The method of claim 1, wherein said level of basicity of composition B consists of a mild level of basicity.

6. The method of claim 5, wherein said mild level of basicity corresponds to about 5.0% of alkalizing compound by weight of composition B.

7. The method of claim 1, wherein said level of basicity of composition B consists of a regular level of basicity.

8. The method of claim 7, wherein said regular level of basicity corresponds to about 6.0% of alkalizing compound by weight of composition B.

9. The method of claim 1, wherein said level of basicity of composition B consists of a strong level of basicity.

10. The method of claim 9, wherein said strong level of basicity corresponds to about 7.0% of alkalizing compound by weight of composition B.

11. The method of claim 1, wherein said alkalizing compound is selected from the group consisting of ammonium hydroxide, monoisopropanol amine, monoethanolamine, aminoethylpropanol, potassium hydroxide, sodium hydroxide and mixtures thereof.

12. The method of claim 1, wherein said oxidizing compound is an inorganic oxidizing compound selected from the group consisting of hydrogen peroxide, inorganic alkali metal peroxide compounds, inorganic perhydrate salt oxidizing compounds, melanine peroxide, sodium perborate and sodium percarbonate.

13. The method of claim 1, wherein said compositions A, B and C are mixed according to a ratio of about 1:1:2 by weight of the mixture.

14. A kit for personalizing the permanent modification of a color of a type of keratinous fibres of a person, the kit comprising:
   a first container containing a composition A, said composition A comprising from about 0.01% to about 10% of a reducing agent and from 0 to 10% of a coloring compound by weight of composition A,
   a second container containing a composition B, said composition B comprising an alkalizing compound, wherein composition B has a level of basicity selected from mild, regular and strong, and
   a third container containing a composition C, said composition C comprising from about 1.5% to about 12% of an oxidizing compound by weight of composition C.

15. The kit of claim 14, wherein said reducing agent consists in a thio compound.

16. The kit of claim 14, wherein said reducing agent is selected from the group consisting of cysteamine HLC, ammonium thioglycolate and ammonium thiolactate.

17. The kit of claim 14, wherein said coloring compound is selected from the group consisting of dye intermediates, direct dyes and mixtures thereof.

18. The kit of claim 14, wherein said mild level of basicity corresponds to about 5.0% of alkalizing compound by weight of composition B.

19. The kit of claim 14, wherein said regular level of basicity corresponds to about 6.0% of alkalizing compound by weight of composition B.

20. The kit of claim 14, wherein said strong level of basicity corresponds to about 7.0% of alkalizing compound by weight of composition B.

21. The kit of claim 14, wherein said alkalizing compound is selected from the group consisting of ammonium hydroxide, monoisopropanol amine, monoethanolamine, aminoethylpropanol, potassium hydroxide, sodium hydroxide and mixtures thereof.

22. The kit of claim 14, wherein said oxidizing compound is an inorganic oxidizing compound selected from the group consisting of hydrogen peroxide, inorganic alkali metal peroxide compounds, inorganic perhydrate salt oxidizing compounds, melanine peroxide, sodium perborate and sodium percarbonate.

* * * * *